United States Patent [19]

Hogt et al.

[11] Patent Number: 5,202,386
[45] Date of Patent: Apr. 13, 1993

[54] MODIFICATION OF (CO)POLYMERS EMPLOYING ORGANIC PEROXIDES

[75] Inventors: Andreas H. Hogt, Enschede; John Meijer, Deventer; Peter Hope, Twello; Jernej Jelenic, Deventer, all of Netherlands

[73] Assignee: Akzo NV, Arnhem, Netherlands

[21] Appl. No.: 703,965

[22] Filed: May 22, 1991

Related U.S. Application Data

[62] Division of Ser. No. 283,676, Dec. 13, 1988, Pat. No. 5,037,892.

[30] Foreign Application Priority Data

Dec. 14, 1987 [NL] Netherlands .................. 8703014
Dec. 6, 1988 [EP] European Pat. Off. ......... 88202797.2

[51] Int. Cl.$^5$ ................................................ C08F 8/00
[52] U.S. Cl. ..................................... 525/298; 525/391; 525/392
[58] Field of Search ....................... 525/298, 391, 392

[56] References Cited

U.S. PATENT DOCUMENTS

2,516,649 7/1950 Rust et al.
4,705,888 11/1987 Meijer et al.
4,774,293 9/1988 Beijleveld et al.
4,833,209 5/1989 Beijleveld et al.
4,837,287 6/1989 Meijer.

FOREIGN PATENT DOCUMENTS

8503477 1/1985 PCT Int'l Appl.

OTHER PUBLICATIONS

R. C. Keller, "Peroxide Curing of Ethylene—Propylene Elastomers", *Rubber and Chemical Technology*, vol. 61, pp. 238-254.
W. Hoffman, "Crosslinking Agents in Ethylene-Propylene Rubbers", *Progress in Rubber and Plastics Technology*, vol. 1, No. 2, pp. 18-50, (1985).
M. Tomoi et al., "Synthesis and Crosslinking of Polystyrenes Containing a Pendant Epoxy Group", *Makromol. Chem., Rapid Commun.*, 7, pp. 143-148, (1986).
F. Svec et al., "Reactive Polymers I.", *Die Angewandte Makromolekulare Chemie*, 48, pp. 135-143, (1975).
E. Montaudon et al., "Addition Radicalaire au Peroxyde d'Allyle et de T-Butyle: Synthese d'e'Poxydes Fonctionnels", *Bull. Soc. Chim. France*, pp. 198-202, (1985) and English-language translation.
"Incorporation of Amine Antioxidants into Natural Rubber Netwok Via Epoxide Groups", *Journal of Polymer Science: Polymer Letters Edition*, vol. 22, pp. 327-334, (1984).
A. Ravve et al., "Studies on Graftin Glycidyl Methacrylate on Polyvinyl Chloride Backbones", *Journal of Polymer Science*, vol. 61, pp. 185-194, (1962).
C. S. L. Baker et al., "Epoxidized Natural Rubber—a New Synthetic Polymer?", *Rubber World*, 191(6), pp. 15-20, (1985).
"Challenging Time for Natural Rubber", *Rubber Developments*, vol. 38, No. 2, pp. 48-50, (1985).
F. P. Greenspan, "E. Epoxidation", *Chemical Reaction of Polymers*, Chapter II, p. 152 et. seq., (1964).

*Primary Examiner*—Bernard Lipman
*Attorney, Agent, or Firm*—Louis A. Morris

[57] ABSTRACT

Organic (co)polymers, including saturated (co)polymers, are modified by contacting them with an organic peroxide and decomposing the peroxide. Use is made of an organic peroxide having the general formula R—(O—O—CHR$^1$—CR$^2$=CR$^3$R$^4$)N, wherein N is 1, 2 or 3; R$^1$ is H, C$_1$-C$_4$ alkyl or C$_2$-C$_4$ alkylene; R$^2$, R$^3$ and R$^4$ are, independently, H or C$_1$-C$_4$ alkyl; two of the substituents R$^1$-R$^4$ together may form C$_3$-C$_{12}$ alkylene; and, when N is 1, R is an optionally hydroxyl substituted C$_4$-C$_{18}$ T.alkyl, P-menth-8-yl, C$_5$-C$_{18}$ T.alkenyl, 1-vinylcyclohexyl or a group of the formula: —C(CH$_3$)2—C$_6$HJ(5—M)—R$^5$(M), wherein M is 0, 1 or 2 and R$^5$ is isopropenyl or 2-hydroxyisopropyl; when N is 2, R is a C$_8$-C$_{12}$ alkylene or alkynylene group having a tertiary structure at both ends, or a group having the formula —(C)CH$_3$)2)2—C$_6$H(4—X)—R$^5$(X), wherein X is 0 or 1; and when N is 3, R is 1,2,4- or 1,3,5-triisopropylbenzene-alpha, alpha"-triyl, i.a., 3-allylperoxy-3,3-dimethylpropene according to a preferred embodiment the modification is carried out in the presence of a coagent, whereby the advantageous polymer properties, such as adhesion to polar materials, are further enhanced.

3 Claims, No Drawings

MODIFICATION OF (CO)POLYMERS EMPLOYING ORGANIC PEROXIDES

This is a division of application Ser. No. 07/283,676 filed Dec. 13, 1988, now U.S. Pat. No. 5,037,892.

The invention relates to a process of modifying (co)polymers employing organic peroxides and to shaped objects comprising the modified (co)polymers.

It is generally known that the introduction of epoxide or other functional groups into the appropriate (co)polymers may lead to improved physical and chemical properties of the (co)polymers. According to Rubber World 191(6) pp. 15-20 (1985) and Rubber Developments, Vol. 38 No. 2, pp. 48-50 (1985), for instance, the introduction of epoxide groups into natural rubber leads to advantages such as an increased glass transition temperature, increased oil resistance, reduced gas permeability, improved resilience, increased tensile strength, and improved adhesion to other materials, such as silica fillers, glass fibers and other polymers, more particularly PVC, which is of importance to the preparation of polymeric blends. Further, the polymers thus modified permit carrying out chemical reactions that are typical of epoxy groups. As examples thereof may be mentioned: i) cross-linking the polymer with polyfunctional compounds containing active hydrogen atoms, such as polyamines and dibasic acids, which is described in Chemical Reactions of Polymers, E. M. Fettes (ed.), Interscience Publications, New York (1964), Chapter II, part E, pp. 152 et. seq., ii) covalently bonding to the polymer of antioxidants having amino groups in the molecule, which is described in Journal of Polymer Science, Polymer Letters Edition, Vol. 22, 327-334 (1984) and iii) reacting with fluorine-containing compounds, such as trifluoroacetic acid, resulting in a polymer with improved lubricity and ozone resistance, which is described in WO 85/03477.

Generally, epoxide groups are introduced into (co)polymers by so-called epoxidation reactions, in which an unsaturated (co)polymer in the form of a latex or dissolved in an organic solvent is brought into reaction with an epoxidizing reagent suitable for unsaturated double bonds, such as a lower aliphatic peroxy carboxylic acid. To this method, however, there are several disadvantages. First of all, the requirement that the (co)polymer should be unsaturated implies that only a very limited number of (co)polymers can be provided with epoxide groups. For instance, the entire group of saturated (co)polymers is excluded from being functionalized by that route. In the second place, the use of solvents implies that the epoxidation reaction must be followed by a purification step. In addition to the drawbacks to such a step from the point of view of processing technique there are the obvious disadvantages to the use of solvents from the point of view of energy consumption and environmental pollution. In the third place, the epoxidation reaction is always attended with side reactions, such as the formation of hydroxyl groups, acyloxy groups, ether groups, keto groups and aldehyde groups, which detracts from the envisaged object of introducing epoxide groups.

Finally, it should be mentioned that it is known to prepare epoxide groups-containing (co)polymers by copolymerizations and graft polymerizations with monomers containing a glycidyl group (cf. Journal of Polymer Science, Vol. 61, pp. 185-194 (1962), Makromol. Chem., Rapid Commun. 7, pp. 143-148 (1986) and Die Angewandte Makromolekulare Chemie 48, pp. 135-143 (1975)). The inevitable attendant formation, however, of undesirable side products, such as the formation of homopolymers of the glycidyl group-containing monomer, is considered a drawback in actual practice. Moreover, these methods permit preparation of only a limited group of modified (co)polymers.

The invention has for its object to eliminate the above drawbacks to the well-known methods of introducing epoxide groups into (co)polymers and to that end it provides a process employing particular organic peroxides for modification of (co)polymers. The organic peroxides correspond to the following formula

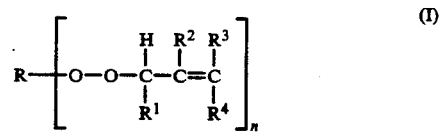

wherein
n=1, 2 or 3
$R^1$ stands for hydrogen, an alkyl group having 1-4 carbon atoms or an alkenyl having 2-4 carbon atoms;
$R^2$, $R^3$ and $R^4$ may be the same or different and represent hydrogen atoms or alkyl groups containing 1-4 carbon atoms;
$R^1$ and $R^2$, $R^1$ and $R^3$, $R^1$ and $R^4$, $R^2$ and $R^3$, $R^2$ and $R^4$, or $R^3$ and $R^4$ form an alkylene having 3-12 carbon atoms.

When n=1
R=a t-alkyl group substituted or not with a hydroxyl group and containing 4-18, preferably 4-12 carbon atoms, p-menth-8-yl, a t-alkenyl group containing 5-18, preferably 5-12 carbon atoms, 1-vinylcyclohexyl or a group of the general formula

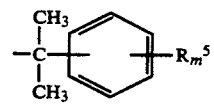

wherein m=0, 1 or 2 and $R^5$ represents an isopropenyl group or a 2-hydroxyisopropyl group;
When n=2,
R=an alkylene group with 8-12 carbon atoms which at both ends has a tertiary structure, an alkynylene group with 8-12 carbon atoms which at both ends has a tertiary structure, a group of the general formula

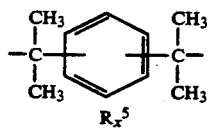

wherein x=0 or 1 and $R^5$ has the above-indicated meaning
When n=3
R=1,2,4-triisopropylbenzene-α, α',α''-triyl or 1,3,5-triisopropylbenzene-α,α',α''-triyl;

The alkyl groups, alkenyl groups and alkylene groups may be linear or branched, unless otherwise indicated. In view of sterical requirements it should be noted that when there is an aromatic ring in the molecule (see above with n=1 and n=2), the ring substituents must in the case of disubstitution not be in a position ortho relative to each other and in the case of trisubstitution not be in three adjacent positions.

It should be added that from Bull. Soc. Chim. France No. 2, 198–202 (1985) t-butyl allyl peroxide is known in itself and that mention is made in this publication of this peroxide being capable of 2,3-epoxypropanating organic solvents with labile hydrogen atoms As solvents are mentioned cyclohexane, tetrahydrofuran, propionic acid, propionic anhydride, methyl propionate, acetonitrile and chloroform. The article also mentions the need for the presence of an auxiliary initiator having a decomposition temperature lower than that of the t-butyl allyl peroxide But this article does not disclose the present invention.

From U.S. Pat. No. 2,516,649 compounds are known in themselves of the general formula

wherein
$R_1$ = a tertiary organic radical
$R_2$ = represents an unsaturated aliphatic or cyclic aliphatic radical, more particularly allyl tertiary-butyl peroxide, allyl tertiary-amyl peroxide, allyl-α,α-dimethylbenzyl peroxide, and methallyl tertiary-butyl peroxide.

According to said Patent Specification the above allyl compounds may be used as catalysts for the polymerization of conjugated or non-conjugated polyunsaturated compounds.

THE PEROXIDES

The peroxides according to the invention correspond to the above-described formula (I) and are selected from the class of the dialkyl peroxides. They may be prepared in the usual manner. In preparing dialkyl peroxides use may be made of a primary or a secondary alkenyl derivative of the general formula

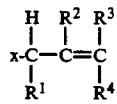

wherein $R^1$–$R^4$ have the above-indicated meaning and x represents Cl, Br,

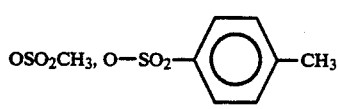

or a different leaving group.

As examples of suitable starting compounds may be mentioned:

allyl bromide; (2-propenyl bromide),
2-methyl-2-propenyl bromide; (methylallyl bromide),
1-methyl-2-propenyl bromide,
1-ethyl-2-propenyl bromide,
1-propyl-2-propenyl bromide,
1-isopropyl-2-propenyl bromide,
2-t-butyl-2-propenyl bromide,
2-neopentyl-2-propenyl bromide,
2-butenyl bromide,
1-methyl-2-butenyl brmide,
3-methyl-2-butenyl bromide,
2,3-dimethyl-2-butenyl bromide,
1,2,3-trimethyl-2-butenyl bromide,
2-cyclohexenyl bromide On account of its readily being available use is preferably made of allyl bromide. In the preparation of the present dialkyl peroxides a primary or secondary alkenyl halide II can be reacted in a usual way in an alkaline medium with a hydroperoxide in the presence of a phase transfer catalyst.

As examples of suitable hydroperoxides may be mentioned:

1,1-dimethyl-2-propenyl hydroperoxide,
1-methyl-1-ethyl-2-propenyl hydroperoxide,
1,1-diethyl-2-propenyl hydroperoxide,
1-methyl-1-isopropyl-2-propenyl hydroperoxide,
1,1-diisopropyl-2-propenyl hydroperoxide,
t-butyl hydroperoxide,
1,1-dimethyl butyl hydroperoxide,
1,1,3,3-tetramethyl butyl hydroperoxide,
1,1-dimethyl-3-hydroxybutyl hydroperoxide,
t-pentyl hydroperoxide,
1-ethenyl-1-hydroperoxycyclohexane,
1-(1-hydiroperoxy-1-methyl ethyl)-4-(1-hydroxy-1-methyl ethyl)benzene,
1-(1-hydroperoxy-1-methyl ethyl)-4-methyl cyclohexane,
(1-hydroperoxy-1-methyl ethyl)benzene; (α-cumyl hydroperoxide),
1,3-di(1-hydroperoxy-1-methyl-1-ethyl)-benzene,
1,4-di(1-hydroperoxy-1-ethyl)benzene
1,3,5-tri(1-hydroperoxy-1-methyl-1-ethyl)benzene,
2,5-dimethyl-2,5-dihydroperoxyhexane,
2,5-dimethyl-2,5-dihydroperoxy-3-hexyne.

As typical examples of dialkyl peroxides for use according to the invention may be mentioned:

3-allyl peroxy-3,3-dimethyl propene,
3-(1-methyl-2-propenyl peroxy)-3,3-dimethyl propene,
2-allyl peroxy-2-methyl propane,
2-(1-methyl-2-propenyl peroxy)-2-methyl propane,
1-allyl peroxy-1,1-dimethyl butane,
1-allyl peroxy-1,1,3,3-tetramethyl butane,
1-allyl peroxy-1,1-dimethyl-3-hydroxybutane,
1-allyl peroxy-1,1-dimethyl propane,
1-(1-methyl-2-propenyl peroxy)-1,1-dimethyl propane,
1-(1-allyl peroxy-1-methyl ethyl)-4-methyl cyclohexane,
(1-(2-methyl-2-propenyl peroxy)-1-methyl-1-phenyl) ethane,
(1-allyl peroxy-1-methyl-1-phenyl) ethane,
(1-(1-methyl-2-propenyl peroxy)-1-methyl-1-phenyl) ethane,
1,3-di(1-allyl peroxy-1-methyl-1-ethyl) benzene,
1,4-di(1-allyl peroxy-1-methyl-1-ethyl) benzene,
1,3,5-tri(1-allyl peroxy-1-methyl-1-ethyl) benzene,
2,5-di(allyl peroxy)-2,5-dimethyl hexane,
2,5-di(allyl peroxy)-2,5-dimethyl-3-hexyne,
(1-(2-cyclohexenyl peroxy-1-methyl-1-phenyl) ethane.

The peroxides can be prepared, transported, stored and applied as such or in the form of powders, granules, solutions, aqueous suspensions or emulsions, pastes, etc.

Which of these forms is to be preferred partly depends on the ease of feeding the peroxide into closed systems. Also considerations of safety (desensitizing) may play a role. As examples of suitable desensitizing agents may be mentioned solid carrier materials, such as silica, chalk and clay, inert plasticizers or solvents, such as mono- or dichloro benzene, and water.

MODIFICATION OF (CO)POLYMERS

The present peroxides are excellently suitable for use in the preparation of epoxide groups-containing (co)polymers, in which process a "non-modified" (co)polymer is brought into contact with the peroxide, upon which the peroxide will be entirely or almost entirely decomposed. The peroxide may be brought into contact with the (co)polymer in various ways, depending on the object of the modification. If, for instance, epoxide groups are to be present on the surface of a (co)polymeric object, the peroxide may be applied to the surface of the material to be modified. It will often be desirable for epoxide groups to be homogeneously distributed in the (co)polymeric matrix. In that case the peroxide may be mixed with the material to be modified, which material may either be in the molten state, solution or, in the case of an elastomer, in the plastic state; to this end use may be made of conventional mixers, such as kneaders, internal mixers and (mixing) extruding equipment. Should the mixing be impeded by a too high melting temperature of the (co)polymer -because of premature peroxide decomposition- it is recommended that first of all the (co)polymer in the solid state should be provided with epoxide groups by contacting with the present peroxides, after which the modified material is melted and the epoxide groups will be homogeneously distributed in the matrix. Alternatively the (co)polymer may be dissolved first, and the reaction with the present peroxides be carried in solution.

An important practical aspect of the invention is that the moment the peroxide and the (co)polymer are brought into contact with each other and also the moment the peroxide is to be decomposed can be chosen independently of other usual (co)polymer processing steps, such as introducing additives, shaping, etc. First of all, for instance, epoxide groups may be introduced into a (co)polymer employing a peroxide and subsequently additives may be introduced, after which the product may be mould processed. However, it is also possible, for instance, for the peroxide to be added to the (co)polymer along with other additives and to decompose the peroxide in a following shaping step at elevated temperature, such as extrusion, compression moulding, blow moulding or injection moulding. The sole restriction here applies to certain (co)polymers which in the end are to be cross-linked. In the case of such (co)polymers care should be taken that the peroxide is in any case present in the (co)polymer prior to cross-linking.

Examples of suitable (co)polymers which according to the invention can be modified by means of epoxide groups are saturated (co)polymers, such as polyethylene, e.g. LLDPE, MDPE, LDPE and HDPE, polypropylene, both isotactic and atactic, ethylene/vinylacetate copolymer, ethylene/ ethylacrylate copolymer, ethylene/methylacrylate copolymer, ethylene/methylmethacrylate copolymer, chlorinated polyethylene, fluorrubber, silicone rubber, polyurethane, polysulphide, polyacrylate rubber, ethylene/propylene copolymer, polyphenylene oxides, nylon, polyesters, such as polyethylene terephthalate and polybutylene terephthalate, polycarbonates, copolyetheresters, poly(butene-1), poly(butene-2), poly(isobutene), poly(methylpentene), polyvinyl chloride, polyvinyl chloride/vinylacetate graft copolymer, polyvinyl chloride/acrylonitrile graft copolymer, and combinations thereof; and unsaturated (co)polymers, such as polybutadiene, polyisoprene, poly(cyclopentadiene), poly(methylcyclopentadiene), partly dehydrochloridated polyvinyl chloride, butadiene/styrene copolymer, acrylonitrile/butadiene/styrene terpolymer, ethylene/propylene/dienemonomer terpolymer, isoprene/styrene copolymer, isoprene/isobutylene copolymer, isoprene/styrene/acrylonitrile terpolymer, polychloroprene, butadiene/acrylonitrile copolymer, natural rubber, and combinations thereof. Also combinations of saturated and unsaturated polymers can be modified according to the invention. In general, any (co)polymer comprising abstractable hydrogen atoms can be employed in the present process.

It has been found that by contacting certain (co)polymers with the present peroxides also degradation of the polymer chains occurs, which may affect the mechanical properties of the modified (co)polymer. Particularly those polymers prone to the formation of tertiary carbon radicals under the conditions of peroxide decomposition tend to undergo degradation. Examples of (co)polymers liable to degradation are polyisobutylene, poly($\alpha$-methyl)-styrene, polymethacrylates, polymethacrylamide, polyvinylidene chloride, polypropylene, in particular isotactic polypropylene, and polyvinyl/alcohol. According to a preferred embodiment of the invention the present modification is conducted in the presence of a coagent. A coagent is generally understood to be a usually polyfunctional reactive additive e.g. a polyunsaturated compound for use in cross-linking of (co)polymers, which additive will react very rapidly with polymer radicals, will overcome steric hindrance effects and will minimize undesirable side reactions. For further information about coagents or sometimes called coactivators it is referred to Rubber Chemistry and Technology, Vol. 61, pp. 238-254 and W. Hofmann, Progress in Rubber and Plastics Technology, Vol. 1, No. 2, March 1985, pp. 18-50. In relation to the present invention the expression "coagent" has the same meaning. A wide variety of coagents is commercially available such as di-and triallyl compounds, di- and tri(meth)acrylate compounds, bismaleimide compounds, divinyl benzene, vinyl toluene, vinyl pyridine, parachinone dioxime, 1,2-cis-polybutadiene and their derivatives. Furthermore, mention should be made of oligomers or polymers of aromatic compounds having at least two alkenyl substituents, such as oligomers of 1,3-diisopropenyl benzene, 1,4-diisopropenyl benzene, 1,3,5-triisopropenyl/benzene. Incorporating an effective amount of a coagent into the (co)polymer prior to or during the reaction with the present peroxides, will avoid the reduction of the mechanical properties and sometimes even result in an improvement. Surprisingly this use of a coagent further provides an enhauced adhesion strength of the resulting modified (co)polymers to substrates of a more polar nature This enhancement of the adhesive properties may be attributable to a higher efficiency of the epoxide-groups introduction according to the invention, when additionally coagents are present. However, the inventors do not wish to be bound by this theory.

Also in modifying (co)polymers less liable to undergo degradation it appeared advantageous to include a coagent during the modification reaction, since the efficiency of the introduction of epoxide-groups could be increased in this way. Such polymers generally being cross-linked under the action of peroxides are, for example, polyethylene, atactic polypropylene, polystryren, polyacrylates, polyacrylamides, polyvinylchloride, polyamides, aliphatic polyesters, polyvinylpyrrolidone, unsaturated rubbers, polysiloxanes, ethylene propylene rubbers, ethylene propylene diene rubbers and their copolymers. Due to the invention the favourable effect on the physical and chemical properties as a result of the presence of epoxide groups, which has so far been limited to a relatively small group of (co)polymers (see the introductory part of the description), can now also be obtained with a large group of other (co)polymers.

Particularly suitable (co)polymers to be modified by way of the invention are polyethylene, polypropylene, and ethylene/propylene copolymer, ethylene/vinylacetate copolymer, ethylene/propylene/dienemonomer terpolymer.

The peroxide according to the invention is generally used in an amount of 0.01 to 15% by weight, preferably 0.1 to 10% by weight, and more particularly 1 to 5% by weight, calculated on the weight of the (co)polymer. Use also may be made of combinations of peroxides according to the invention. Also of advantage may be the presence of an auxiliary peroxide having a decomposition temperature lower than that of the peroxide according to the invention.

The temperature at which the modification is carried out is generally in the range of 50° to 350° C., preferably 100° to 250° C., care being taken then that in order to obtain optimum results the duration of the modification step under the given conditions is at least five half-life periods of the peroxide.

As mentioned above, the (co)polymer may in addition also contain usual additives. As examples for such additives may be mentioned: stabilizers, such as inhibitors against oxidative, thermal and UV degradation, lubricants, extender oils and pH controlling substances, such as calcium carbonate, release agents, colorants, reinforcing or non-reinforcing fillers, such as silica, clay, chalk, carbon black and fibrous materials, nucleating agents, plasticizers, accelerators, crosslinking agents, such as peroxides and sulphur. These additives may be employed in the usual amounts.

The invention is further described in the following examples.

EXAMPLE 1

Preparation of 2-allyl peroxy-2-methyl propane (peroxide 1)

To a mixture of 0.1 mole of powdered KOH, 0.02 moles of benzyl triethyl ammonium chloride and 100 ml of methylene chloride stirred at 5°–10° C. was added over a period of 35 minutes a mixture of 0.1 mole of t-butyl hydroperoxide, 0.1 mole of allyl bromide, and 70 ml of methylene chloride. After the temperature had increased to 20° C., the reaction mixture was stirred for 4 hours at this temperature. Following filtration the methylene chloride solution was concentrated by evaporation under reduced pressure. To the residue were added 60 ml of pentane. The organic layer was washed three times with 15 ml of an aqueous solution of 10% by weight of potassium hydroxide and then with water to pH 7. The organic layer was dried with anhydrous sodium sulphate and concentrated by evaporation under reduced pressure. Obtained were 7.3 g of colourless liquid having a peroxide 1 content determined by G.L.C. of 95%.

Preparation of 3-allyl peroxy-3,3-dimethyl propene (peroxide 2)

The peroxide 2 was prepared using the same procedure as described for peroxide 1, except that use was made of 1,1-dimethyl-2-propenyl hydroperoxide instead of t-butyl hydroperoxide.

Obtained after treatment were 11.0 g of colourless liquid having a peroxide 2 content determined by G.L.C. of 91%.

Preparation of (1-allyl peroxy-1-methyl-1-phenyl) ethane (peroxide 3)

The procedure was the same as described for peroxide 1, except that use was made of (1-hydroperoxy-1-methyl-1-phenyl) ethane instead of t-butyl hydroperoxide.

Obtained after treatment were 10.3 g of colourless liquid having a peroxide 3 content determined by G.L.C. of 86%.

Preparation of 2,5-dimethyl-2,5-di(allyl peroxy)hexane (peroxide 4)

The preparation of peroxide 4 was carried out in a manner analogous to that for peroxide 1, use being made of 0.05 moles of 2,5-dimethyl-2,5-dihydroperoxyhexane, 1.0 mole of allyl bromide, and 35 ml of tetrahydrofuran. Obtained after treatment were 8.4 g of colourless liquid having a peroxide 4 content determined by G.L.C. of 62%

Prior to the modification tests the peroxides 1–4 were further purified by column chromatography. After treatment the content of each of the peroxides was determined by G.L.C. Of each of the peroxides 1–4 the structure was confirmed by NMR and IR spectroscopic analyses.

Table I gives for each peroxide the peroxide content and the temperatures at which the half-life periods of decomposition are 10 hours, 1 hour, and 0.1 hour (0.1 M solution in chlorobenzene).

Preparation of (1-methallylperoxy-1-methyl-1-phenyl) ethane (peroxide 5)

To a mixture of 0.11 moles of KOH, 11 ml water and 0.005 moles of tetrabutyl ammonium chloride stirred at 10° C. was added over a period of 30 minutes a mixture of 0.10 moles (1-hydroperoxy-1-methyl-1-phenyl) ethane and 0.10 moles methallylbromide. After the temperature had been increased to 20° C. over a period of 45 minutes, 25 ml of water were added and the organic supernatant layer was separate off. To the organic layer were added 50 ml of petroleum ether (60–80) followed by two washings with 100 ml water. The organic layer was dried with anhydrous sodium sulphate and concentrated by evaporation under reduced pressure. Obtained were 19.0 g of colourless liquid having a peroxide 5 content determined by G.L.C. of 84%.

Preparation of (1-crotylperoxy-1-methyl-1-phenyl) ethane (peroxide 6)

The peroxide 6 was prepared using the same procedure as described for peroxide 5, except that use was made of crotyl bromide instead of t-butylhydroperoxide.

Obtained were 19.9 g of pale yellow liquid having a peroxide 6 content dermined by G.L.C. of 89%.

TABLE 1

| Peroxide[a] | Content % | Temperature (°C.) for t½ of | | |
|---|---|---|---|---|
| | | 10 hours | 1 hours | 0.1 hour |
| 1 | 95 | 113 | 133 | 156 |
| 2 | 91 | 100 | 123 | 149 |
| 3 | 95 | 108 | 128 | 149 |
| 4 | 95 | 103 | 125 | 150 |
| 5 | 84 | 104 | 122 | 143 |
| 6 | 89 | 113 | 129 | 147 |

[a]
1 = 2-allyl peroxy-2-methyl propane
2 = 3-allyl peroxy-3,3-dimethyl propene
3 = (1-allyl peroxy-1-methyl-1-phenyl) ethane
4 = 2,5-dimethyl-2,5-di(allyl peroxy) hexane
5 = (1-methallylperoxy-1-methyl-1-phenyl) ethane
6 = (1-crotylperoxy-1-methyl-1-phenyl) ethane.

EXAMPLE 2

Modification of Polyethylene

Use being made of the 6 peroxides described in Example I, polyethylene (Lupolen 1810H) was modified in a 50 ml-Brabender blender at a speed of 30 rotor revolutions per minute for 60 minutes. The amount of peroxide in each experiment and the reaction temperatures are listed in Table 1. Table 2 also gives the epoxide contents of the resulting polymers.

The epoxide content was determined as follows:

In a 250 ml-round bottomed flask about 1 g of product, which had been weighed out to the nearest 1 mg, was dissolved with refluxing in 100 ml of xylene. After the mixture had been cooled to 30° C., 10,00 ml of a solution in 1,4-dioxane of 4N HCl were added, after which the mixture was kept at 50° C. for 48 hours. Subsequently, 50 ml of acetone, 50 ml of water and 5 ml of 4N nitric acid were added with stirring, after which the mixture was titrated potentiometrically, with stirring, with 0.01 N silver nitrate, use being made of a combined Ag, AgCl electrode.

TABLE 2

| Peroxide[a] | Concentration mmoles/100 g pol. | Reaction Temperature °C. | Epoxide content mmoles/100 g pol. |
|---|---|---|---|
| 1 | 20 | 148–164 | 4.8 |
| 2 | 20 | 151–161 | 6.1 |
| 3 | 20 | 151–163 | 7.4 |
| 4 | 10 | 152–162 | 2.4 |
| 5 | 20 | 185 | 3.8 |
| 6 | 20 | 174 | 3.5 |

[a]for indentification of the peroxides, see Table 1.

EXAMPLE 3

Modification of poly-(2,6-dimethylphenylene oxide) with peroxide 1

In a 300 ml open reactor 11 g of 2,6-dimethylpolyphenylene oxide were mixed with 0.58 g peroxide 1, which reaction mixture was made up to a total volume of 100 ml with monochloro benzene. The duration of the treatment was 6 hours at a temperature of 131° C. under continuous argon pressure.

The modified polymer was isolated by adding the reaction mixture to vigorously stirred petroleum ether (60-80) followed by filtration of the precipitated polymer. The polymer obtained was vacuum-dried for 17 hours at 70° C.

The epoxide content was determined as described in Example 2 and was found to be 11.0 mmoles of epoxy /100 g polymer.

EXAMPLE 4

Modification of Polypropylene in the Presence of 1,3-Diisopropenyl Benzene Oligomer Preparation of 1,3-diisopropenyl benzene oligomer To 498 g of 1,3-diisopropenyl benzene were added 1200 ml of heptane and 2 g of p-toluene sulfonic acid 1 aq followed by stirring for 30 min. at 80° C. Thereupon the reaction mixture was successively washed with 200 ml of NaOH 2N and water until neutral. The organic layer containing heptane and non-reacted 1,3-diisopropenyl benzene was evaporated at 100° C. and 0.1 mbar. Obtained were 169 g of clear viscous oil.

Modification

In a Haake Rheomix ® 500 electrically heated mixing chamber with a capacity of 53 g the peroxide as prepared in Example 1 and oligo-1,3-diisopropenyl benzene were intermixed in the amounts given in Table 3 with polypropylene (Hostalen ® PPU 0180 P, MFI (190° C.; 2.16 kg)=6.3 g/10 min, ex. Hoechst) at a speed of 30 rpm and over a period of 15 min. at a temperature of 180° C., the given amounts of peroxide and oligo-1,3-diipropenyl benzene being calculated on the percentage by weight of polypropylene. During the reaction torque versus time was registrated with a Haake Reocord ® system 40 from which the torque-after-10 minutes (M10) was derived.

The modified polymer was granulated in a Retch ® granulator by using a 6 mm sieve. Use being made of a Fonteyn ® press the granulate was formed into 1×125×200 mm plates between nylar polyester foil under the following conditions: temp. 180° C.; 1 min. without pressure; 1 min. 4-8 KPa; 3 min. 41-61 KPa; 9 min. cooling with water.

Tensile strength (TS) and elongation at break (EB) were measured in conformity with ISO method R 257, use being made of a Zwich ® tensile tester 1474. Moreover, the peel strength of a bi-component lacquer (2 K-PUR Decklack, ex Akzo Coatings, 2 K-PUR Hardener, ex Akzo Coatings) was determined according to ASTM D 429-81. The two component coating was prepared by mixing the 2 K-PUR-Hardener with 2 K-PUR-Decklack in a mixing ration 3:1 parts per weight (pot-life - 8h). Application to sample by dip coating. Stoving conditions were flash off time (20° C.)=10 min; object temperature 90° C.; time 40 min. Test pieces of dimensions 130 mm×25 mm were used one end being covered with 1 cm adhesive tape, whereupon the coating was applied as described. A dip coated polyamide gasket was applied and the coating was dried as described.

The 180° peel strength was determined according to ASTM-D 429-81 using a Zwick tensile tester 1474 at. 25 mm/min. Besides indicating the nature of failure the peel strength is reported as (average peel force)/(diameter test pieces). Also the lap shear strength (LSS) was measured using an epoxy resin having the following composition: 10 g of bisphenol A/F epoxy resins (Epikote ® DX 235, ex Shell), 6 g of polyaminoamide (Epilink 177; ex. Akzo Chemicals) and 0.08 g of silan A 174 (ex. Union Carbide). A thin film of resin was applied to the adhesion surface area (20×15 mm) of a modified polymer plate (40×20×1 mm). Another modified polymer plate was placed on the adhesion surface area and the two parts were firmly clamped together to avoid occlusion of air. This composition was kept in a stove for 72 hours of 30° C.

The lap shear strength was determined in a Zwick ® Tensile tester 1474 by measuring the force (kg/cm²) needed to separate the plates from each other at a speed of 25 mm/min. In case the adhesion fails by shifting apart of the two pieces of polymer, the measured force is a measure for adhesion of the epoxyresin. In case the polymer breaks before the adhesion fails the force at which the adhesion will fail is not measurable but it will be higher than the force needed for polymer breakage The values obtained are given in Table 3. Also given are the results of a comparative experiment conducted in the absence of the 1,3-diisopropenyl benzene oligomer.

TABLE 3

| nr. | Peroxide m.mol/ 100 g polymer | oligo M-DIPB (phr) | M10 (mg) | TS (MPa) | EB (%) | LSS (kg/cm²) | Peel strength ×10⁻² (N/mm) |
|---|---|---|---|---|---|---|---|
|  | — | — | 598 | 41 | 40 | 0 | 1 ± 1 |
|  | 2 | — | <50 | ND² | ND² | —² | ND² |
| 3 | 20 | 2.5 | 538 | 23 | 30 | >7.3¹ | 32 ± 1 |
| 4 | 10 | 2.5 | 457 | 39 | 50 | >9.4¹ | 71 ± 5 |

¹polymer breakage
²not measurable

From the values of Table 3 it will be clear that polypropylene modified in the absence of diisopropenyl benzene is not suitable to be further processed. As compared with unmodified polypropylene the modified polypropylene displays improved adhesion properties which are of major importance to the affinity for paint of polypropylene, the production of polymer blends, composites and filled polymers.

EXAMPLE 5

Adhesion to Modified Low Density Polyethylene (LDPE)

LDPE (Lupolen 1810 H, MFI (190° C.; 2.16 kg)=1,3-1.8 g/10 min, ex BASF) was modified with peroxide 3 and in another experiment with peroxide 4 in the way described in the first part of Example 2 Each resulting polymer was compressed into a plate 1 mm thick over a period of 15 min. and at a temperature of 160° C. Subsequently, of each plate the peel strength of a bi-component lacquer and the lap shear strength (LSS) using an epoxy resin was measured in the way described in Example 4, which also mentions the results of a comparative experiment conducted with unmodified LDPE. The results clearly show that the adhesion obtained with modified polymers according to the invention is greater than that with unmodified LDPE.

TABLE 4

| nr. | Peroxide mmol/100 g polymer | LSS kg/cm² | Peel strength ×10⁻² N/mm |
|---|---|---|---|
| — | 0 | 2.2 | nihil |
| 3 | 5 | 2.3 | 4 |
| 3 | 10 | 3.9 | 3 |
| 3 | 20 | 5.1 | 6 |
| 3 | 40 | 6.0 | 6 |
| 4 | 5 | 4.6 | 5 |
| 4 | 10 | 4.5 | 5 |
| 4 | 20 | >4.9¹ | 12 |

TABLE 4-continued

| nr. | Peroxide mmol/100 g polymer | LSS kg/cm² | Peel strength ×10⁻² N/mm |
|---|---|---|---|
| 4 | 40 | >5.3¹ | 12 |

¹polymer breakage

We claim:
1. An epoxide group-containing (co)polymer prepared by the process for modifying (co)polymers employing an organic peroxide wherein said peroxide is brought into contact with the (co)polymer and the peroxide is decomposed, said peroxide being an organic peroxide of the general formula

$$R \left[ -O-O-\underset{R^1}{\overset{H}{\underset{|}{C}}}-\underset{|}{\overset{R^2}{C}}=\underset{|}{\overset{R^3}{C}}-R^4 \right]_n \quad (I)$$

wherein
n=1, 2 or 3
$R^1$ stands for hydrogen, an alkyl group having 1–4 carbon atoms or an alkenyl having 2–4 carbon atoms; and
$R^2$, $R^3$ and $R^4$ may be the same or different and represent hydrogen atoms or alkyl groups containing 1–4 carbon atoms;
when n=1
R=
 a t-alkyl group substituted or not with a hydroxyl group and containing 4–18 carbon atoms, p-menth-8-yl,
 a t-alkenyl group containing 5–18 carbon atoms, 1-vinylcyclohexyl or
 a group of the general formula $$-\underset{\underset{CH_3}{|}}{\overset{CH_3}{\underset{|}{C}}}-\underset{}{\bigcirc}-R_m^5$$

wherein m=0, 1 or 2 and $R^5$ represents an isopropenyl group or a 2-hydroxyisopropyl group;
when n=2,
R=
 an alkylene group with 8–12 carbon atoms which at both ends has a tertiary structure,
 an alkynylene group with 8–12 carbon atoms which at both ends has a tertiary structure, or
 a group of the general formula

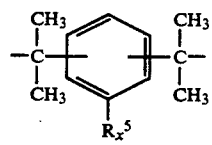

wherein x=0 or 1 and $R^5$ has the above-indicated meaning when n=3,
R=
1,2,4-triisopropylbenzene-$\alpha,\alpha',\alpha''$-triyl or
1,3,5-triisopropylbenzene-$\alpha,\alpha',\alpha''$-triyl.

2. A shaped object manufactured with an epoxide group-containing (co)polymer of claim 1.

3. A shaped object manufactured with two or more (co)polymers, of which at least one is a (co)polymer of claim 1.

* * * * *

UNITED STATES PATENT AND TRADEMARK OFFICE
CERTIFICATE OF CORRECTION

PATENT NO. : 5,202,386
DATED : April 13, 1993
INVENTOR(S) : HOGT, Andreas H., et al.

It is certified that error appears in the above—identified patent and that said Letters Patent is hereby corrected as shown below:

Column 4, line 1, please change "brmide" to -- bromide --;
Column 4, line 32, please change "(1-hydroperoxy-1-methyl ethyl)benjzene;" to -- (1-hydroperoxy-1-methyl ethyl)benzene; --;
Column 6, line 63, after "nature" please insert -- . --;

Column 9, lines 1/2, please change "t-butylhydroperoxide" to -- methallylbromide --; and
Column 11, line 47, after "Example 2" please insert -- . --.

Signed and Sealed this

Fourth Day of July, 1995

Attest:

BRUCE LEHMAN

Attesting Officer    Commissioner of Patents and Trademarks